(12) United States Patent
Lee

(10) Patent No.: US 6,297,198 B1
(45) Date of Patent: Oct. 2, 2001

(54) ISOXAZOLE DERIVATIVES AND THEIR USE AS HERBICIDES

(75) Inventor: Shy-Fuh Lee, Sunnyvale, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 08/841,737

(22) Filed: Apr. 29, 1997

Related U.S. Application Data

(63) Continuation of application No. 08/744,910, filed on Nov. 8, 1996, now abandoned, which is a continuation of application No. 08/645,942, filed on May 14, 1996, now abandoned.

(51) Int. Cl.$^7$ .................. A01N 43/80; C07D 261/10
(52) U.S. Cl. .................................... 504/271; 548/243
(58) Field of Search .................. 504/271; 548/243

(56) References Cited

U.S. PATENT DOCUMENTS

| | | | | |
|---|---|---|---|---|
| 3,852,298 | * | 12/1974 | Wagner et al. | 504/261 |
| 4,618,617 | | 10/1986 | Yamamoto | 514/364 |
| 4,699,916 | | 10/1987 | Sirrenberg et al. | 514/364 |
| 5,041,618 | | 8/1991 | Brand et al. | 560/104 |
| 5,201,932 | | 4/1993 | Maywald et al. | 504/271 |
| 5,366,957 | * | 11/1994 | Cain et al. | 504/271 |
| 5,489,570 | * | 2/1996 | Geach et al. | 504/261 |

FOREIGN PATENT DOCUMENTS

| | | | |
|---|---|---|---|
| 3326509 | | 7/1983 | (DE) . |
| 3821503 | | 6/1988 | (DE) . |
| 002881 | | 10/1978 | (EP) . |
| 132680 | | 7/1984 | (EP) . |
| 171739 | | 8/1985 | (EP) . |
| 359547 | | 9/1989 | (EP) . |
| 418175 | * | 9/1990 | (EP) . |
| 418667 | | 9/1990 | (EP) . |
| 452002 | | 3/1991 | (EP) . |
| 470856 | | 8/1991 | (EP) . |
| 487357 | | 11/1991 | (EP) . |
| 496630 | * | 1/1992 | (EP) . |
| 527036 | | 8/1992 | (EP) . |
| 527037 | | 8/1992 | (EP) . |
| 560482 | | 2/1993 | (EP) . |
| 560483 | | 2/1993 | (EP) . |
| 580439 | | 7/1993 | (EP) . |
| 588357 | | 9/1993 | (EP) . |
| 603712 | | 12/1993 | (EP) . |
| 609797 | | 1/1994 | (EP) . |
| 609798 | | 1/1994 | (EP) . |
| 625505 | * | 5/1994 | (EP) . |
| 636622 | | 7/1994 | (EP) . |
| 2193495 | | 2/1988 | (GB) . |
| 2228480 | | 8/1990 | (GB) . |
| 2263638 | | 8/1993 | (GB) . |
| 2284547 | | 6/1995 | (GB) . |
| 2293380 | | 3/1996 | (GB) . |
| 9220642 | | 5/1991 | (WO) . |
| 9215579 | | 9/1991 | (WO) . |
| 9115479 | | 10/1991 | (WO) . |
| 9414782 | | 7/1994 | (WO) . |
| 9418179 | | 8/1994 | (WO) . |
| 9515691 | | 6/1995 | (WO) . |
| 9516678 | | 6/1995 | (WO) . |
| 9522903 | | 8/1995 | (WO) . |
| 9522904 | | 8/1995 | (WO) . |
| 9524403 | | 9/1995 | (WO) . |
| 9526956 | | 10/1995 | (WO) . |
| 9531446 | | 11/1995 | (WO) . |
| 9603877 | | 2/1996 | (WO) . |
| 9604274 | | 2/1996 | (WO) . |
| 96/03977 | * | 2/1996 | (WO) . |
| 9615673 | | 5/1996 | (WO) . |
| 9617519 | | 6/1996 | (WO) . |
| 9621357 | | 7/1996 | (WO) . |
| 9623785 | | 8/1996 | (WO) . |
| 9626192 | | 8/1996 | (WO) . |

\* cited by examiner

*Primary Examiner*—Joseph K. McKane
(74) *Attorney, Agent, or Firm*—William A. Teoli, Jr.

(57) ABSTRACT

Compounds defined by the generic formula

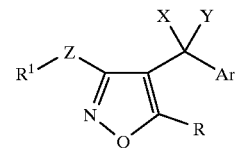

or an agriculturally acceptable salt thereof, wherein the letter R represents a lower alkyl, haloalkyl, alkoxyalkyl, cycloalkyl, or alkenyl, each of which is optionally substituted, the symbol $R^1$ represents a lower alkyl, haloalkyl or phenyl group, optionally substituted, X and Y are each independently a hydrogen, hydroxyl, halogen, cyano, alkylsulfenyl, alkylsulfinyl, alkylsulfonyl, acyloxy, carbamoyloxy, alkylsulfonyloxy, amino, substituted amino, acylamino, sulfamoyloxy, sulfamyl, or X and Y can be combined to be =O, —S(CH$_2$)$_m$S— and —O(CH$_2$)$_m$O—, in which m is 2 or 3, the symbol Ar represents an aromatic ring moiety optionally substituted with from one to four groups and wherein two substituents on adjacent positions of the aromatic ring may be taken together with the two atoms to which they are attached, to form a 5- to 7-membered ring optionally substituted, and the letter Z represents —S—, —SO— or —SO$_2$—, exhibit herbicidal activity.

8 Claims, No Drawings

ISOXAZOLE DERIVATIVES AND THEIR USE AS HERBICIDES

This is a CONTINUATION of application Ser. No. 08/744,910, filed on Nov. 8, 1996, now abandoned which is a CONTINUATION of application Ser. No. 08/645,942, filed on May 14, 1996, now abandoned.

BACKGROUND OF THE INVENTION

Various substituted isoxazoles are known to be useful as herbicides. Typical herbicidal properties of such compounds are described in U.S. Pat. No. 5,489,570 and European Patent Application with Pub. No. 0 418 175 A2.

SUMMARY OF THE INVENTION

This invention relates to a novel class of isoxazole derivatives and their use as herbicides when used in a phytotoxic amount. More specifically, this invention relates to isoxazole derivatives having the formula:

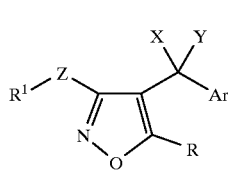

(I)

or an agriculturally acceptable salt thereof

In the above formula, the letter R represents a lower alkyl, haloalkyl, alkoxyalkyl, cycloalkyl, or alkenyl, each of which is optionally substituted.

The symbol $R^1$ represents a lower alkyl, haloalkyl or phenyl group, optionally substituted. X and Y are each independently a hydrogen, hydroxyl, halogen, cyano, alkylsulfenyl, alkylsulfinyl, alkylsulfonyl, acyloxy, carbamoyloxy, alkoxy, alkoxycabonyl, alkylsulfonyloxy, amino, substituted amino, acylmino, sulfamoyloxy, sulfamyl; or X and Y can be combined to be =O, —S(CH$_2$)$_m$S— and —O(CH$_2$)$_m$O—, in which m is 2 or 3.

The symbol Ar represents an aromatic ring moiety optionally substituted with from one to four groups. Additionally, two substituents on adjacent positions of the aromatic ring may be taken together with the two atoms to which they are attached, to form a 5- to 7-membered ring optionally substituted.

The letter Z represents —S—, —SO— or —SO$_2$—.

The compounds of the present invention, as will be seen from the data which follows, have utility as both pre-emergence and post-emergence herbicides, against a wide range of plant species.

DETAILED DESCRIPTION OF THE INVENTION

Abbreviations and Definitions

The following abbreviations are used herein: AcOH, acetic acid; Boc, t-butoxycarbonyl; DME, dimethoxyethane; DMF, dimethylformamide; EtOAc, ethyl acetate; NMP, N-methylpyrrolidone; TFA, trifluoroacetic acid.

As used herein, the term "alkyl" refers to a saturated hydrocarbon radical which may be straight-chain or branched-chain (for example, ethyl, isopropyl, t-amyl, or 2,5-dimethylhexyl) or cyclic (for example cyclobutyl, cyclopropyl or cyclopentyl) and contains of from 1 to 24 carbon atoms. This definition applies both when the term is used alone and when it is used as part of a compound term, such as "haloalkyl" and similar terms. Preferred alkyl groups are those containing 1 to 6 carbon atoms, which are also referred to as "lower alkyl." All numerical ranges in this specification and claims are intended to be inclusive of their upper and lower limits.

The term "alkenyl" as used herein refers to an alkyl group as described above which contains one or more sites of unsaturation.

The term "alkoxy" refers to an alkyl radical as described above which also bears an oxygen substituent which is capable of covalent attachment to another hydrocarbon radical (such as, for example, methoxy, ethoxy and t-butoxy).

The term "aryl" or "aromatic ring moiety" refers to an aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

By the term "agriculturally acceptable salts" is meant salts the cations of which are known and accepted in the art for the formation of salts for agricultural or horticultural use. Preferably the salts are water-soluble. Suitable acid addition salts formed by compounds of formula I include salts with inorganic acids, for example hydrochlorides, sulphates, phosphates and nitrates and salts with organic acids, for example acetic acid.

The term "herbicide", as used herein, means a compound which controls or modifies the growth of plants. By the term "herbicidally effective amount" is meant an amount of compound which causes a modifeing effect upon the growth of plants. The term "plants" is meant to include germinant seeds, emerging seedlings and established vegetation, including roots and above ground portions. Such modifying effects include all deviations from natural development, for example, killing, retardation, defoliation, desiccation, regulation, stunting, tillering, stimulation, leaf burn, dwarfing and the like.

Isoxazole Derivatives

The compounds of the present invention are represented by the formula:

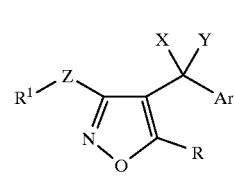

(I)

or an agriculturally acceptable salt thereof.

In the above formula, the letter R represents a lower alkyl, haloalkyl, alkoxyalkyl, cycloalkyl, or alkenyl, each of which is optionally substituted with —SR$^2$ or —OR$^2$, in which R$^2$ is a lower alkyl group. In preferred embodiments, R is a lower alkyl, haloalkyl or cycloalkyl, more preferably cycloalkyl. In the most preferred embodiments, R is cyclopropyl.

The symbol $R^1$ represents a lower alkyl, haloalkyl or phenyl group, optionally substituted. Suitable substituents include lower alkyl, lower haoialkyl, halogen and nitro. In preferred embodiments, $R^1$ is lower alkyl and lower haloalkyl.

The letters X and Y are each independently a hydrogen, hydroxyl, halogen, cyano, alkylsulfenyl, alkylsulllnyl, alkylsulfonyl, acyloxy, carbamoyloxy, alkoxy, alkoxycarbonyl, alkylsulfonyloxy, amino, —$NR^3R^4$, acylamino, sulfamoyloxy, sulfamyl; or X and Y can be combined to be =O, —$S(CH_2)_mS$— and —$(CH_2)_mO$—, in which m is 2 or 3. Preferably, X and Y are combined to be =O, —$S(CH_2)_mS$— and —$O(CH_2)_mO$—, in which m is 2 or 3. More preferably, X and Y are combined to be =O.

The symbol Ar represents an aromatic ring moiety optionally substituted with from one to four groups which are each independently halogen, lower alkyl, haloalkyl, lower alkoxy, lower haloalkoxy, lower alkoxyalkyl, lower alkylthioalkyl, lower alkylsulfonylalkyl, lower alkylsulfinylalkyl, $R^3S$—, $R^3SO$—, $R^3SO_2$—, $R^3SO_3$—, nitro, cyano, lower alkoxyalkoxy, —$COR^4$, —$CO_2R^4$, —$CR^5(=NOR^4)$, —$NR^5SO_2R^4$, —$NR^4R^6$, or —$NR^3R^4$. Preferably, the groups are halogen, lower alkyl, lower haloalkyl, lower alkoxy, lower haloalkoxy, $R^3S$—, $R^3SO$—, $R^3SO_2$—, nitro, —$NR^5SO_2R^4$, —$NR^4R^6$, or —$NR^3R^4$. Additionally, two substituents on adjacent positions of the aromatic ring may be taken together with the two atoms to which they are attached, to form a 5- to 7-membered ring optionally substituted. Preferably, two substituents on adjacent positions of the aromatic ring, when attached, will form a 6-member ring.

The symbol $R^3$ represents a lower alkyl, haloalkyl, or (substituted)phenyl in which the substituents are preferably lower alkyl or halogen; $R^4$ is hydrogen or lower alkyl: $R^5$ represents a hydrogen, lower alkyl, alkenyl, alkynyl, cycloalkyl or (substituted)phenyl; and $R^6$ represents —$COR^4$ or $CO_2R_4$.

The letter Z represents —S—, —SO— or —$SO_2$—.

Compound Preparation

The compounds of the present invention can be prepared by a synthetic scheme as outlined in FIG. 1. β-diketones (I in FIG. 1) can be prepared according to known literature methods (see, for example, Trebs, et al., *Chef Ber.* 87:1163 (1954); Hauser et al. ORGANC REACTIONS 8:59 (1954); and Rathke, etal., *J. Org. Chem.* 50:2622 (1985)). Conversion of the β-diketones to ketene dithioacetals II (R=lower alkyl) can be carried out based on known procedures described in Villemin, et al., *Synthesis* 301 (1991), Pak, et al., *Synthesis* 793 (1988) and Augustin, et al., *Tetrahedron* 32:3055 (1976). For those embodiments in which R=(substituted)phenyl in III, transketalization of II is carried out using (substituted)thiophenol at room temperature or at elevated temperature in organic solvents such as ethanol, tetrahydrofuran, and dimethylformamide. Conversion of the sulfide group to a corresponding suyoxide or sulfone can be accomplished using a variety of oxidation methods, for example, with meta-chloroperbenzoic acid or peracetic acid.

Methods of Application

Application of a compound of formula I is made according to conventional procedures to the weeds or their locus using a herbicidally effective amount of the compound, usually from 1 g to 10 kg/ha.

Compounds according to the invention may be used for the control of both broadleaf and grassy weeds in both preplant incorporation and pre- and post-emergent application. Compounds may also exhibit selectivity in various crops and may thus be suited for use in weed control in crops such as but not limited to corn, cotton, wheat, soybean and rice.

The optimum usage of a compound of formula I is readily determined by one of ordinary skill in the art using routine testing such as greenhouse testing and small plot field testing. It will depend on the compound employed, the desired effect (a phytotoxic effect requiring a higher rate than a plant growth regulating effect), the conditions of treatment and the like. In general satisfactory phytotoxic effects are obtained when the compound of formula I is applied at a rate in the range of from 0.001 to 5.0 kg, more preferably of from 0.05 to 2.5 kg per hectare, especially 0.01 to 2.5 kg per hectare.

The compounds of formula I may be advantageously combined with other herbicides for broad spectrum weed control. Examples of herbicides which can be combined with a compound of the present invention include those selected from carbamates, thiocarbamates, chloroacetamides, triazines, dinitroanilines, benzoic acids, glycerol ethers, pyridazinones, uracils, phenoxys and ureas for controling a broad spectrum of weeds.

The compounds of formula I are conveniently employed as herbicidal compositions in association with agriculturally acceptable diluents. Such compositions also form part of the present invention. They may contain, aside from a compound of formula I as active agent, other active agents, such as herbicides or compounds having antidotal, fungicidal, insecticidal or insect attractant activity. They may be employed in either solid or liquid forms such as a wettable powder, an emulsifiable concentrate, a granule or a microcapsule incorporating conventional diluents. Such compositions may be produced in conventional manner, for example by mixing the active ingredient with a diluent and optionally other formulating ingredients such as surfactants.

Agriculturally acceptable additives may be employed in herbicidal compositions to improve the performance of the active ingredient and to reduce foaming, caking and corrosion, for example.

The term "diluent" as used herein means any liquid or solid agriculturally acceptable material which may be added to the active constituent to bring it in an easier or improved applicable form, respectively, to a usable or desirable strength of activity. It can for example be talc, kaolin, diatomaceous earth, xylene or water.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

Particular formulations to be applied in spraying forms such as water dispersible concentrates or wettable powders may contain surfactants such as wetting and dispersing agents, for example the condensation product of formaldehyde with naphthylene sulphonate, an ethoxylated alkylphenol and an ethoxylated fatty alcohol.

In general, the formulations include from 0.01 to 99% by weight of active agent and from 0 to 20% by weight of agriculturally acceptable surfactant, and from 0.1 to 99.99% of solid or liquid diluent(s) the active agent consisting either of at least one compound of formula I or mixtures thereof with other active agents. Concentrate forms of compositions generally contain between about 2 and 95%, preferably between about 10 and 90% by weight of active agent.

Typical herbicidal compositions, according to this invention, are soluble powders, wettable powders, water dispersible granules, microcapsule suspensions and emulsifiable concentrates. Descriptions are provided below in which the quantities are in parts by weight.

(a) Preparation of a Soluble Powder

The water soluble salts of this invention can be hammer milled to a screen size of 100 mesh. The resulting powder will readily dissolve in water for spraying.

(b) Preparation of a Wettable Powder

25 Parts of a compound according to this invention are mixed and milled with 25 parts of synthetic fine silica, 2 parts of sodium lauryl sulphate, 3 parts of sodium lignosulfonate and 45 parts of finely divided kaolin until the mean particle size is about 5 micron. The resulting wettable powder is diluted with water to a desired concentration.

(c) Preparation of Water Dispersible Granule

40 Parts of a water insoluble parent acid compound according to this invention are wet milled in a solution of 10 parts MARASPERSE® N-22 (a sodium lignosulfonate) and 50 parts water until a median particle size of 5 micron is reached. The slurry is spray dried on a NIRRO MOBILE MINOR unit at an inlet temperature of 150° C. and outlet temperature of 70° C. The resulting granule can be readily dispersed in water for application.

(d) Preparation of a Microcapsule Suspension 0.38 Parts of a VINOL® 205 (a partially hydrolyzed polyvinyl alcohol) are dissolved in 79.34 parts water.

3.75 Parts of an organic soluble parent acid compound according to this invention are dissolved in 3.75 parts TENNECO® 500-100 (a xylene range aromatic solvent). To this solution are added 0.63 parts of SEBACOYL CHLORIDE and 0.88 parts PAPI® 135 (polymethylene isocyanate).

1.89 Parts piperazine and 0.50 parts of NaOH are dissolved in 12.60 parts of water.

Transfer premix (a) to a one quart esterizer and while stirring add premix (b) and sheer for approximately 60 seconds or until a droplet size of 10–20 microns is reached. Immediately add premix (c), continue stirring for 3 hours and neutralize with acetic acid. The resulting capsule suspension may be diluted in water for spraying.

(e) Preparation of an Emulsifiable Concentrate

13 Parts of an organic soluble parent acid compound according to this invention are dissolved in 79 parts of TENNECO® 500-100 along with 2 parts TOXIMUL® RHF and 6 parts TOXIMUL® S. TOXIMUL®s are a "matched pair"; each containing anionic and nonionic emulsifiers. The stable solution will spontaneously emulsify in water for spraying.

The foregoing description and the following examples are offered primarily for illustration and not as limitations. It will be readily apparent to those of ordinary skill in the art that the operating conditions, materials, procedural steps and other parameters of the system described herein may be further modified or substituted in various ways without departing from the spirit and scope of the invention.

EXAMPLES

Example 1

This example describes the preparation of 5-cyclopropyl-3-methylthio-4-(2-chloro-4-methylsulfonylbenzoyl) isoxazole.

To a solution of 3-cyclopropyl-2-(bis(methylthio) methylene)-1-(2-chloro-4-methylsulfonylphenyl)propan-1, 3-dione (123 mg, 0.304 mmol) in ethanol (15 mL) was added hydroxylamine hydrochloride (23 mg, 0.334 mmol) and sodium acetate (25 mg, 0.304 mmol). The resulting mixture was stirred at r.t. overnight, then evaporated to dryness and the residue was taken up in ethyl acetate, washed with water, dried and evaporated to dryness. The crude product was purified by preparative Thin-layer chromatography to give 90 mg of crystalline 5-cyclopropyl-3-methylthio-4-(2-chloro-4-methylsulfonylbenzoyl)isoxazole, m.p. 141° C.

Example 2

This example describes the preparation of 4-methoxy-5,8-dimethyl-6-(5-cyclopropyl-3-methylthioisoxazoyl) thiachroman-1,1-dioxide.

A mixture of 4-methoxy-5,8-dimethyl-6-(3-cyclopropyl-2-(bis(methylthio)methylene)-1,3-dioxo-propyl) thiachroman-1,1-dioxide (454 mg, 1.00 mmol), hydroxylanine hydrochloride (78 mg, 1.12 mmol) and sodium acetate (92 mg, 1.12 mmol) in ethanol (10 mL) was stirred at r.t. overnight, then diluted with dichloromethane, washed with brine, dried and evaporated. The crude product was crystalized from ether/hexane (2.5/1) to give 380 mg of 4-methoxy-5,8-dimethyl-6-(5-cyclopropyl-3-methylthioisoxazoyl) thiachroman-1,1-dioxide, m.p. 140° C.

Example 3

This example describes the preparation of 5-cyclopropyl-3-methylsulfonyl-4-(2-chloro-4-methylsulfonylbenzoyl) isoxazole.

To a solution of 5-cyclopropyl-3-methylthio-4-(2-chloro-4-methylsulfonylbenzoyl)isoxazole (377 mg, 1.015 mmol) in dichloromethane (30 mL) was added 3-chloroperbenzoic acid (400 mg, 57–86%). The resulting mixture was stirred at r.t. overnight, then diluted with dichloromethane, washed with aqueous sodium bisulfite, aqueous sodium bicarbonate, brine dried and evaporated to dryness. The crude product was purified by preparative thin-layer chromatography to give crystalline 5-cyclopropyl-3-methylsulfonyl-4-(2-chloro-4-methylsulfonylbenzoyl)isoxazole (380 mg), mp. 150° C.

Example 4

This example describes the preparation of 5-cyclopropyl-3-methylsulfinyl-4-(2-methyl-4-methylsulfonylbenzoyl) isoxazole and 5-cyclopropyl-3-methylsulfonyl-4-(2-methyl-4-methylsulfonylbenzoyl)isoxazole.

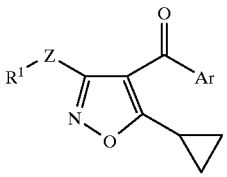

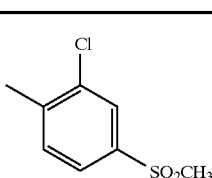

To a solution of 5-cyclopropyl-3-methylthio-4-(2-methyl-4-methylsulfonylbenzoyl)isoxazole (750 mg, 2.127 mmol) in dichloromethane (35 mL) was added 3-chloroperbenzoic acid (650 mg, 57–87%, Aldrich). The resulting mixture was stirred at r.t. for 2 hours, then diluted with dichloromethane, washed with aqueous sodium bicarbonate, brine, dried and evaporated to dryness. The crude product was purified by preparative thin-layer chromatography to give crystalline 5-cyclopropyl-3-methylsulfinyl-4-(2-methyl-4-methylsulfonylbenzoyl)isoxazole (436 mg), rp. 147° C. and 5-cyclopropyl-3-methylsulfonyl-4-(2-methyl-4-methylsulfonylbenzoyl)isoxazole (378 mg), m.p. 142° C.

In the following table, the above four examples are listed together with additional examples which were prepared in a manner analogous to that described above, starting with the appropriate materials. The compounds in the table are representative of those embodied in the present invention.

TABLE 1

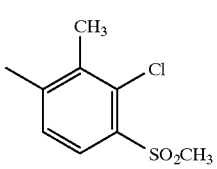

| Compound Number | m.p. (° C.) | R¹ | Ar | Z |
|---|---|---|---|---|
| 1 | 141 | Me | 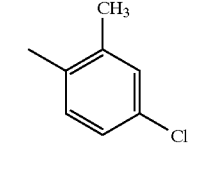 | —S— |
| 2 | 136 | Me | 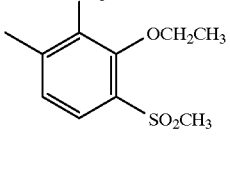 | —S— |
| 3 | 88 | Me | 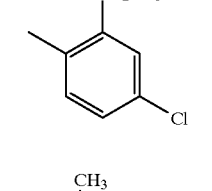 | —S— |
| 4 | 154–156 | Me | 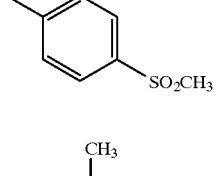 | —S— |
| 5 | 156 | Me | 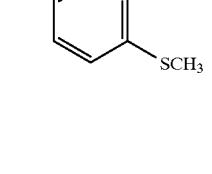 | —S— |
| 6 | 140 | Me |  | —S— |
| 7 | 117 | Me |  | —S— |

TABLE 1-continued
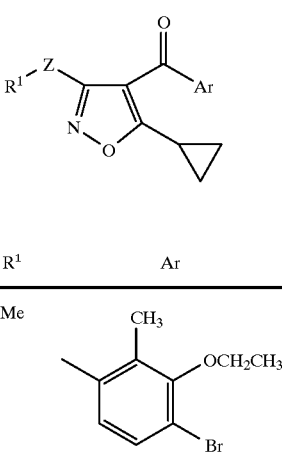
| Compound Number | m.p. (° C.) | R¹ | Ar | Z |
|---|---|---|---|---|
| 8 | oil | Me | 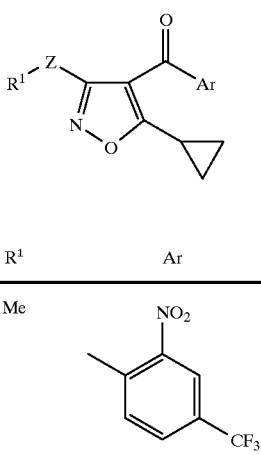 | —S— |
| 9 | oil | Me | 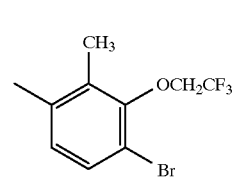 | —S— |
| 10 | 150 | Me | 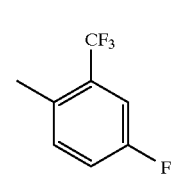 | —S— |
| 11 | 142 | Me | 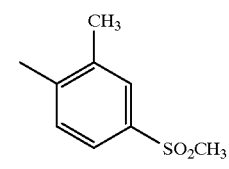 | —SO₂— |
| 12 | 147 | Me |  | —SO— |
| 13 | 150 | Me | 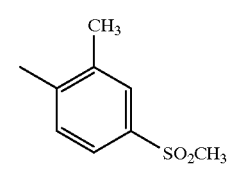 | —SO₂— |
| 14 | 142 | Me | 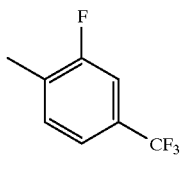 | —S— |
| 15 | 127 | Me | 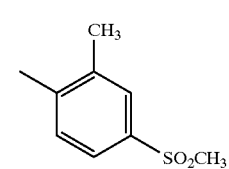 | —S— |
| 16 | 70–72 | Me | 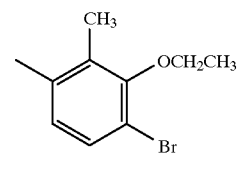 | —S— |
| 17 | oil | Et |  | —S— |
| 18 | 78–80 | Me | 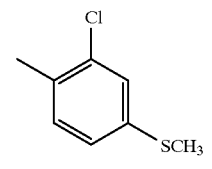 | —S— |
| 19 | oil | Me | 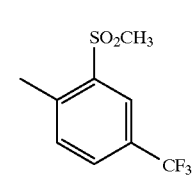 | —SO₂— |
| 20 | 101 | Me | 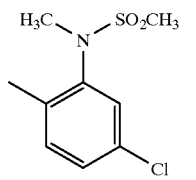 | —S— |
| 21 | — | Me |  | —S— |

TABLE 1-continued

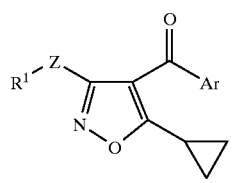

| Compound Number | m.p. (° C.) | R¹ | Ar | Z |
|---|---|---|---|---|
| 22 | — | Me | (2-methyl-5-(N-methyl-methanesulfonamido)-4-trifluoromethylphenyl) | —S— |
| 23 | — | Me | (4-chloro-3-(N-methyl-methanesulfonamido)-4-methylphenyl) | —S— |
| 24 | — | Me | (3-chloro-2-methyl-6-methoxycarbonyl-4-methanesulfonylphenyl) | —S— |
| 25 | — | Me | (5,6-dimethyl-8-methyl-4-(methoxyimino)-thiochroman-1,1-dioxide) | —S— |
| 26 | — | Me | (5,6-dimethyl-8-methyl-4-methoxy-thiochroman-1,1-dioxide) | —S— |

TABLE 1-continued

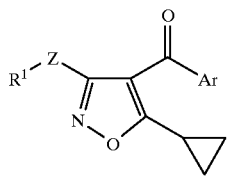

| Compound Number | m.p. (° C.) | R¹ | Ar | Z |
|---|---|---|---|---|
| 27 | 129–130 | Me | 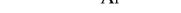 | —S— |

Example 5

This example illustrates the general procedures for pre- and post-emergence the compounds of the present invention.

5.1 Stock Solutions

The test compounds were weighed and dissolved in a stock solution consisting Of acetone:deionized water (1:1) and 0.5% adjuvant mixture. Dilutions from this stock solution were performed to allow for preparation of spray solutions consisting of single doses applied at a level equivalent to either 1.0 or 0.25 kg/ha of active ingredient. The solutions were applied by a linear track sprayer set to deliver 1000 L/ha spray volume.

5.2 Pre-emergence Studies

In pre-emergent studies, each dose of herbicide was applied as a band treatment over the seed zone. Pots containing the seeds were then top-dressed with soil the plants were grown in the greenhouse and visually evaluated 7 and 19 days after treatment.

5.3 Post-emergence Studies

In post-emergence studies, each dose of compound was applied to the foliage of the selected weed seedling species. The plants were allowed to grow in the greenhouse and visually evaluated at 1, 7 and 19 days after treatment.

5.4 Herbicidal Evaluation

Herbicidal control was evaluated as % injury with 100% injury considered complete control and 0% considered no control Table 2 depicts the results of injury on weed species evaluated at 19 days after treatment in pre- and post-emergence studies at an application rate of 1.0 kg/ha active ingredient.

The selected weed species used to evaluate the effectiveness of the compounds include velvetleaf (Abutiol thiophrasti, ABUTH), redroot pigweed (Amaranthus retroflexus, AMARE), mustard white (Sinapis alba, SINAL), black nightshade (Solanum nigrum, SOLNI), wild oat (Avena fatua, AVEFA), downy brome (Bromus tectorum, BROTE), barnyardgrass (Echinochloa crus-galli, ECHCG), and green foxtail (Setaria viridis, SETVI).

TABLE 2

Herbicide Injury Data (1 kg/ha)

| Compound | Pre Post | Monocots | | | | Dicots | | | |
|---|---|---|---|---|---|---|---|---|---|
| | | ECHCG | SETVI | AVEFA | BROTE | SINAL | AMARE | SOLNI | ABUTH |
| 1 | | 100 | 100 | 100 | 65 | 100 | 100 | 100 | 100 |
|   | | 100 | 75  | 100 | 20 | 100 | 100 | 100 | 100 |
| 2 | | 100 | 100 | 100 | 100 | 100 | 100 | 100 | 100 |
|   | | 100 | 100 | 100 | 50 | 100 | 100 | 100 | 100 |
| 3 | | 100 | 100 | 20 | 10 | 0 | 0 | 30 | 50 |
|   | | 100 | 70 | 50 | 0 | 60 | 50 | 100 | 80 |
| 4 | | 100 | 100 | 90 | 50 | 100 | 100 | 100 | 100 |
|   | | 100 | 100 | 60 | 30 | 100 | 100 | 100 | 100 |
| 5 | | 100 | 100 | 100 | 100 | 100 | 100 | 100 | 100 |
|   | | 100 | 100 | 100 | 100 | 100 | 100 | 100 | 100 |
| 6 | | 100 | 100 | 100 | 55 | 100 | 100 | 100 | 100 |
|   | | 100 | 60 | 80 | 40 | 100 | 100 | 100 | 100 |
| 7 | | 100 | 100 | 45 | 30 | 65 | 100 | 100 | 100 |
|   | | 100 | 55 | 60 | 45 | 100 | 100 | 100 | 100 |
| 8 | | 100 | 55 | 35 | 30 | 50 | 95 | 100 | 60 |
|   | | 100 | 20 | 40 | 10 | 60 | 70 | 100 | 100 |
| 9 | | 100 | 100 | 70 | 80 | 35 | 100 | 100 | 45 |
|   | | 100 | 60 | 50 | 100 | 60 | 100 | 100 | 100 |
| 10 | | 100 | 100 | 100 | 80 | 100 | 100 | 100 | 100 |
|    | | 100 | 100 | 100 | 55 | 100 | 100 | 100 | 100 |
| 11 | | 100 | 100 | 100 | 80 | 100 | 100 | 100 | 100 |
|    | | 100 | 100 | 100 | 45 | 100 | 100 | 100 | 100 |
| 12 | | 100 | 100 | 100 | 100 | 100 | 100 | 100 | 100 |
|    | | 100 | 100 | 100 | 60 | 100 | 100 | 100 | 100 |
| 13 | | 100 | 100 | 100 | 100 | 100 | 100 | 100 | 100 |
|    | | 100 | 100 | 100 | 30 | 100 | 100 | 100 | 100 |
| 14 | | 100 | 100 | 100 | 95 | 100 | 100 | 100 | 100 |
|    | | 100 | 100 | 100 | 55 | 100 | 100 | 100 | 100 |
| 15 | | 100 | 100 | 100 | 80 | 100 | 100 | 100 | 100 |
|    | | 100 | 60 | 100 | 35 | 70 | 100 | 100 | 100 |
| 26 | | 100 | 100 | 100 | 80 | 100 | 100 | 100 | 100 |
|    | | 100 | 100 | 100 | 30 | 100 | 100 | 100 | 100 |
| 27 | | 100 | 100 | 100 | 100 | 100 | 100 | 100 | 100 |
|    | | 100 | 100 | 100 | 65 | 100 | 100 | 100 | 100 |

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

Synthesis of Isazole derivatives

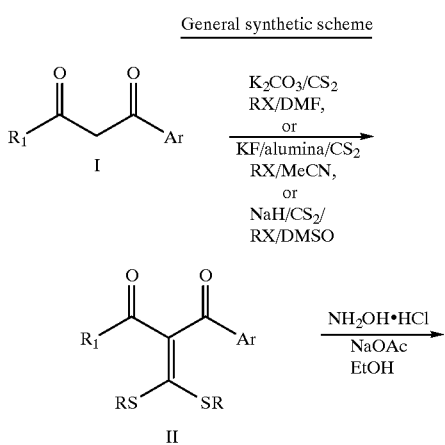

General synthetic scheme

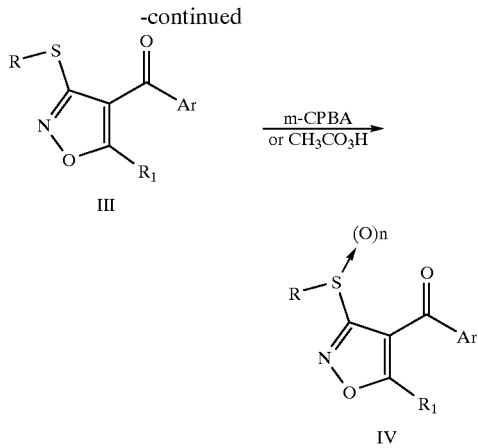

What is claimed is:

1. A compound of the formula:

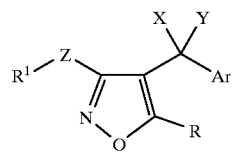

or an agriculturally acceptable salt thereof, wherein:

R is a member selected from the group consisting of lower alkyl, haloalkyl, alkoxyalkyl, cycloalkyl, and alkenyl, each of which is optionally substituted with —$SR^2$ or —$OR^2$;

$R^1$ is a member selected from the group consisting of lower alkyl, haloalkyl and phenyl, optionally substituted;

$R^2$ is lower alkyl;

X and Y are members independently selected from the group consisting of hydrogen, hydroxyl, halogen, cyano, alkylsulfenyl, alkylsulfinyl, alkylsulfonyl, acyloxy, carbamoyloxy, alkoxy, alkoxycarbonyl, alkylsulfonyloxy, amino, substituted amino, acylamino, sulfamoyloxy, sulfamyl; or taken together are selected from the group consisting of =O, —$S(CH_2)_mS$— and —$O(CH_2)_mO$—, in which m is an integer of from 2 to 3;

Ar is an aromatic ring moiety optionally substituted with from one to four substituents independently selected from the group consisting of halogen, lower alkyl, haloalkyl lower alkoxy, lower haloalkoxy, lower alkoxyalkyl, lower alkylthioalkyl, lower alkylsulfonylalkyl, lower alkylsulfinylalkyl, $R^3S$—, $R^3SO$—, $R^3SO_2$—, $R^3SO_3$—, nitro, cyano, lower alkoxyalkoxy, —$COR^4$, —$CO_2R^4$, —$C(=NOR^4)$, —$NR^5SO_2R_4$, —$NR^4R^6$, —$NR^3R^4$, and wherein two substituents on adjacent positions of the aromatic ring, together with the two atoms to which they are attached, form a 5- to 7-membered ring optionally substituted;

$R^3$ is lower alkyl, haloalkyl, or (substituted)phenyl;

$R^4$ is hydrogen or lower alkyl;

$R^5$ is hydrogen, lower alkyl, alkenyl, alkynyl, cycloalkyl or (substituted)phenyl;

$R^6$ is —$COR^4$ or —$CO_2R^4$; and

Z is —S—, —SO— and —$SO_2$—.

2. A compound in accordance with claim 1, wherein

R is a member selected from the group consisting of lower alkyl, haloalkyl, and cycloalkyl;

$R^1$ is a member selected from the group consisting of lower alkyl and haloalkyl, optionally substituted;

X and Y are taken together and are selected from the group consisting of =O, —$S(CH_2)_mS$— and —$O(CH_2)_mO$—, in which m is an integer of from 2 to 3;

Ar is an aromatic ring moiety optionally substituted with from one to four substituents independently selected from the group consisting of halogen, lower alkyl, haloalkyl, lower alkoxy, lower haloalkoxy, $R^3S$—, $R^3SO$—, $R^3SO_2$—, nitro, —$NR^5SO_2R^4$, —$NR^4R^6$, —$NR^3R^4$, and wherein two substituents on adjacent positions of the aromatic ring, together with the two atoms to which they are attached, form a 5- to 7-membered ring optionally substituted.

3. A compound in accordance with claim 1, wherein

R is cycloalkyl;

$R^1$ is a member selected from the group consisting of lower alkyl and haloalkyl;

X and Y are taken together are =O; and

Ar is an aromatic ring moiety optionally substituted with from one to four substituents independently selected from the group consisting of halogen, lower alkyl, haloalkyl, lower alkoxy, lower haloalkoxy, $R^3S$—, $R^3SO$—, $R^3SO_2$—, nitro, —$NR^5SO_2R^4$, —$NR^4R^6$, —$NR^3R^4$, and wherein two substituents on adjacent positions of the aromatic ring, together with the two atoms to which they are attached, form a 5- to 7-membered ring optionally substituted.

4. A compound in accordance with claim 1, wherein R is cyclopropyl, $R^1$ is lower alkyl and X and Y taken together are =O.

5. A compound in accordance with claim 1 which is selected from the group consisting of 5-cyclopropyl-3-methylthio-4-(2-chloro-4-methylsulfonylbenzoyl)isoxazole, 5-cyclopropyl-3-methylthio-4-(4-chloro-2-methylsulfonylbenzoyl)isoxazole, 4-methoxy-5,8-dimethyl-6-(5-cyclopropyl-3-methylthioisoxazoyl)thiachroman-1,1-dioxide, 5-cyclopropyl-3-methylsulfonyl-4-(2-chloro-4-methylsulfonylbenzoyl)isoxazole, 5-cyclopropyl-3-methylthio-4-(3-chloro-2-methyl-4-methylsulfonylbenzoyl)isaxazole, 5-cyclopropyl-3-methylsulfinyl-4-(2-methyl-4-methylsulfonylbenzoyl)isoxazole, 5-cyclopropyl-3-methylthio-4-(2-methylsulfonyl-4-trifluoromethylbenzoyl)isoxazole, 5-cyclopropyl-3-methylthio4-(2-chloro-3-methoxy-4-methylsulfonylbenzoyl)isoxazole and 5-cyclopropyl-3-methylsulfonyl-( 2-methyl-4-methylsulfonylbenzoyl)isoxazole.

6. A herbicidal composition comprising a herbicidally effective amount of a compound of claim 1, or an agriculturally acceptable salt thereof, and at least one member of the group consisting of an agriculturally acceptable carrier and a surface active agent.

7. A herbicidal composition in accordance with claim 6 in the form of an aqueous suspension concentrate, a wettable powder, a water soluble or water dispersible powder, a liquid water soluble concentrate, a liquid emulsifiable suspension concentrate, a granule, or an emulsifiable concentrate.

8. A method for controlling the growth of weeds at a locus which comprises applying to the locus a herbicidally effective amount of a compound of claim 1 or an agriculturally acceptable salt thereof.

* * * * *